US010426391B2

(12) United States Patent
Choon Meng

(10) Patent No.: US 10,426,391 B2
(45) Date of Patent: Oct. 1, 2019

(54) BLOOD COLLECTION CARTRIDGE, BLOOD COLLECTION SYSTEM, AND BLOOD COLLECTION METHOD FOR USE THEREOF

(71) Applicant: Becton, Dickinson and Company, Franklin Lakes, NJ (US)

(72) Inventor: Lau Steven Choon Meng, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 890 days.

(21) Appl. No.: 14/350,926

(22) PCT Filed: Oct. 18, 2012

(86) PCT No.: PCT/US2012/060783
§ 371 (c)(1),
(2) Date: Apr. 10, 2014

(87) PCT Pub. No.: WO2013/059431
PCT Pub. Date: Apr. 25, 2013

(65) Prior Publication Data
US 2015/0173660 A1 Jun. 25, 2015

Related U.S. Application Data

(60) Provisional application No. 61/549,544, filed on Oct. 20, 2011.

(51) Int. Cl.
*A61B 5/153* (2006.01)
*A61B 5/15* (2006.01)
*B01L 3/00* (2006.01)

(52) U.S. Cl.
CPC .......... *A61B 5/153* (2013.01); *A61B 5/15003* (2013.01); *A61B 5/1535* (2013.01);
(Continued)

(58) Field of Classification Search
CPC ........... A61B 5/15-15003; A61B 5/153-1545; A61B 5/150206-150755;
(Continued)

(56) References Cited

U.S. PATENT DOCUMENTS 3,585,984 A 6/1971 Buchanan
3,645,253 A 2/1972 Goverde et al.
(Continued)

FOREIGN PATENT DOCUMENTS

DE 2603777 A1 * 8/1976 ......... A61B 5/15003
GB 2218076 A * 11/1989 .............. B01L 3/502
(Continued)

*Primary Examiner* — Matthew Kremer
(74) *Attorney, Agent, or Firm* — The Webb Law Firm

(57) ABSTRACT

A blood collection cartridge has a distal end, a proximal end, and defines a container interior. The cartridge includes a resealable closure sealing the distal end of the container, having a closure distal end and a closure proximal end. The cartridge also includes a cap sealing the proximal end of the container, having a cap distal end and a cap proximal end. The cartridge further includes a stopper disposed within the container interior sized relative to the container to provide sealing engagement with the sidewall of the container, the stopper having a stopper distal end and a stopper proximal end. A first fluid reservoir is bounded by the sidewall between the closure proximal end and the stopper distal end, and a second fluid reservoir is bounded by the sidewall between the cap distal end and the stopper proximal end. An anticoagulant is disposed within the first fluid reservoir.

21 Claims, 7 Drawing Sheets

(52) U.S. Cl.
CPC .. *A61B 5/150213* (2013.01); *A61B 5/150236* (2013.01); *A61B 5/150251* (2013.01); *A61B 5/150351* (2013.01); *A61B 5/150389* (2013.01); *A61B 5/150496* (2013.01); *A61B 5/150572* (2013.01); *A61B 5/150595* (2013.01); *A61B 5/150732* (2013.01); *A61B 5/150755* (2013.01); *B01L 3/50825* (2013.01); *B01L 2200/16* (2013.01); *B01L 2300/044* (2013.01)

(58) Field of Classification Search
CPC .......... A61B 5/150099; B01L 2200/16; B01L 2300/04–0618; B01L 3/50–502; B01L 3/508–50825; Y10S 220/916
See application file for complete search history.

(56) References Cited

U.S. PATENT DOCUMENTS

| | | | | |
|---|---|---|---|---|
| 3,901,219 A | * | 8/1975 | Kay | B01L 3/5021 422/918 |
| 4,416,290 A | | 11/1983 | Lutkowski | |
| 4,492,634 A | * | 1/1985 | Villa-Real | B01D 33/01 210/359 |
| 2010/0155319 A1 | * | 6/2010 | Felix | B01L 3/50215 210/188 |

FOREIGN PATENT DOCUMENTS

| | | | |
|---|---|---|---|
| GB | 2218076 A | 11/1989 | |
| JP | 5014834 B1 | 5/1975 | |
| JP | 2000189407 A | 7/2000 | |
| JP | 200282120 A | 3/2002 | |
| JP | 2002253535 A | 9/2002 | |
| JP | 2008518679 A | 6/2008 | |
| WO | WO-7900135 A1 * | 3/1979 | .......... B01L 3/50215 |
| WO | 8802238 A1 | 4/1988 | |
| WO | 9216144 A1 | 10/1992 | |

\* cited by examiner

BLOOD COLLECTION CARTRIDGE, BLOOD COLLECTION SYSTEM, AND BLOOD COLLECTION METHOD FOR USE THEREOF

CROSS-REFERENCE TO RELATED APPLICATIONS

This application is the United States national phase of International Application No. PCT/US2012/060783 filed Oct. 18, 2012, and claims priority to U.S. Provisional Patent Application No. 61/549,544 filed Oct. 20, 2011, the disclosures of which are hereby incorporated in their entirety by reference.

BACKGROUND OF THE INVENTION

1. Field of the Disclosure

The present disclosure relates generally to arterial blood collection assemblies. More particularly, the present disclosure relates to an arterial blood collection assembly with a blood collection cartridge and methods for use thereof.

2. Description of the Related Art

Arterial blood collection syringes are used for withdrawing and collecting arterial blood samples from the body of a patient. Once the blood sample is collected, it is subjected to diagnostic analysis for gases, electrolytes, metabolites, and other elements that are indicative of a condition of a patient. Various types of syringes have been devised for collecting arterial blood samples, which mainly comprise elements from a hypodermic syringe, i.e., a plastic or glass syringe barrel, a sealing elastomeric stopper, and a plunger rod. Additionally, certain arterial blood collection syringes include a self-sealing filter that allows passage of air out of the syringe during blood collection, while still preventing the passage of blood. This latter type of syringe having a filter allows for an anaerobic arterial sample to be collected without the need to aspirate the syringe, as is required with a syringe having a plunger rod and a plunger stopper.

Typical arterial blood collection syringes include a two-piece plunger rod assembly comprised of an elastomeric sealing stopper attached to a plunger rod. U.S. Pat. No. 5,314,416 to Lewis et al. discloses a low friction syringe assembly having a typical two-piece plunger rod and a plunger tip assembly. The sealing stopper and plunger rod must be assembled together in a separate operation prior to assembly with a syringe barrel. In addition, a silicone lubricant is usually used on the interior wall of the syringe barrel or the sealing stopper is composed of a self-lubricating polymeric material to facilitate easy slidable movement of the elastomeric sealing stopper against the interior wall of the syringe barrel. Such syringes typically involve an active step for obtaining a blood sample. For example, a needle connected to such a syringe accesses a patient's blood vessel, and the syringe is thereafter aspirated by the user holding the syringe with one hand and drawing the plunger rearwardly within the syringe barrel with the other hand so as to draw a blood sample into the syringe barrel for analysis. The need for the user to use two hands during the blood sample collection introduces unnecessary movement during the blood draw process and might cause discomfort to the patient.

Arterial blood samples can also be obtained passively through the use of a syringe having a plunger with a porous filter to collect blood by way of the blood pressure of a patient from whom the blood is being collected. In such a syringe, the plunger mechanism is typically hollow, and includes a porous filter therein. A separate elastomeric sealing stopper is typically attached to the front end of the plunger mechanism for sealing within the syringe barrel, with air channels in the stopper for air passage through the filter. In use, the plunger is set at a certain position against a graduated scale of the syringe barrel, so that the desired volume of the sample to be collected is represented by the cavity within the syringe. Once a blood vessel of a patient is accessed by an appropriate needle attached to the syringe, arterial blood will fill the syringe under its own pressure. As the cavity within the syringe fills, air within the syringe is allowed to escape from the syringe by way of a gas permeable filter. When the blood sample contacts the filter, the filter seals, thereby preventing escape of blood and ingress of air and other contaminants into the collected sample. U.S. Pat. No. 4,821,738 to Iwasaki et al. discloses an arterial blood gas syringe including a typical two-piece assembly for use. The arterial blood gas syringe is comprised of a plunger rod and an elastomeric sealing plug having channels formed in an upper surface for use in removing air as arterial blood is received in the syringe. The channels extend in a generally radial direction and converge near the center of a sealing plug to allow the passage of air to and through a filter element contained within the sealing plug. U.S. Pat. Nos. 5,377,689 and 5,529,738, both to Mercereau, disclose a sampling syringe including a plunger cap having an air permeable filter attached to a plunger rod, which is in slidable communication with the inner wall of a syringe barrel. However, the arterial blood collected using this type of syringe is exposed to air within the barrel interior of the syringe during the blood collection. This can affect the accuracy of the arterial blood gas analysis since oxygen and carbon dioxide can migrate into or out of the arterial blood sample depending on the partial pressure of gases in the arterial blood relative to atmospheric air.

After completion of the blood sample collection, the needle is removed and the syringe containing the collected blood sample is then transported to the laboratory. Typically blood samples collected in blood collection tubes are transported through pneumatic tubes between the ward and laboratory. However, the plunger that is protruding from the syringe barrel makes handling and transportation of the arterial blood collection syringe difficult and special care has to be taken not to dislodge the plunger thus preventing pneumatic tube transportation and increasing the time and resources required to transport and analyze the collected blood sample.

It would be therefore desirable to provide an arterial blood collection assembly and method of use thereof which is compatible with current clinical practice, which does not expose the collected blood to atmospheric air prior to analysis for blood gas levels.

SUMMARY OF THE INVENTION

The present disclosure provides a blood collection cartridge, a blood collection system, and a method of collecting a blood sample from a blood vessel. The present disclosure provides a blood collection cartridge with a stopper slidably disposed within a container, the stopper sized relative to the container to provide sealing engagement with a sidewall of the container. In one configuration, the stopper contacts the sidewall of the container at a first point and a second point spaced from the first point and no other portion of the stopper contacts the sidewall of the container. In this manner, frictional resistance between the stopper and the container, which restricts movement of the stopper within the interior of the container, only exists at the first point and the second point.

In accordance with an embodiment of the present invention, a blood collection cartridge includes a container having a distal end, a proximal end, and a sidewall extending therebetween and defining a container interior. The blood collection cartridge includes a resealable closure sealing the distal end of the container, the resealable closure having a closure distal end and a closure proximal end, a cap sealing the proximal end of the container, the cap having a cap distal end and a cap proximal end, and a stopper slidably disposed within the container interior of the container, the stopper sized relative to the container to provide sealing engagement with the sidewall of the container, the stopper having a stopper distal end and a stopper proximal end. The blood collection cartridge further includes a first fluid reservoir located within the sidewall between the closure proximal end and the stopper distal end, a second fluid reservoir located within the sidewall between the cap distal end and the stopper proximal end, and an anticoagulant disposed within the first fluid reservoir.

In one configuration, the stopper contacts the sidewall of the container at a first point and a second point spaced from the first point, wherein no other portion of the stopper contacts the sidewall of the container. In another configuration, the presence of arterial blood pressure in the first fluid reservoir forces the stopper to move towards the proximal end of the container. In yet another configuration, the stopper includes at least one sealing ring extending around an outer circumferential surface of the stopper. In one configuration, the stopper includes a first sealing ring and a second sealing ring each extending around an outer circumferential surface of the stopper. In another configuration, the anticoagulant disposed within the first fluid reservoir is in a liquid form. In yet another configuration, the blood collection cartridge includes a spacing member having a protruding portion extending from the distal end of the cap into the container interior. In one configuration, the spacing member is connected to the cap. In another configuration, the cap is rotatable between a closed position in which the cap seals the proximal end of the container and an open position in which the cap breaks the seal with the proximal end of the container allowing air to vent from the container interior.

In accordance with another embodiment of the present invention, a blood collection cartridge includes a container having a distal end, a proximal end, and a sidewall extending therebetween and defining a container interior. The blood collection cartridge includes a resealable closure sealing the distal end of the container, the resealable closure having a closure distal end and a closure proximal end, a cap sealing the proximal end of the container, the cap having a cap distal end and a cap proximal end, and a stopper slidably disposed within the container interior of the container, the stopper sized relative to the container to provide sealing engagement with the sidewall of the container, the stopper having a stopper distal end and a stopper proximal end, the stopper contacting the sidewall of the container at a first point and a second point spaced from the first point, wherein no other portion of the stopper contacts the sidewall of the container. The blood collection cartridge further includes a first fluid reservoir located within the sidewall between the closure proximal end and the stopper distal end, a second fluid reservoir located within the sidewall between the cap distal end and the stopper proximal end, and an anticoagulant disposed within the first fluid reservoir.

In one configuration, frictional resistance between the stopper and the container, which restricts movement of the stopper within the container interior of the container, only exists at the first point and the second point. In another configuration, the first point of the stopper includes a first sealing ring which creates a first seal with the sidewall of the container. In yet another configuration, the second point of the stopper includes a second sealing ring which creates a second seal with the sidewall of the container.

In accordance with another embodiment of the present invention, a blood collection cartridge includes a container having a distal end, a proximal end, and a sidewall extending therebetween and defining a container interior. The blood collection cartridge includes a resealable closure sealing the distal end of the container, the resealable closure having a closure distal end and a closure proximal end, a cap sealing the proximal end of the container, the cap having a cap distal end and a cap proximal end, the cap rotatable between a closed position in which the cap seals the proximal end of the container and an open position in which the cap breaks the seal with the proximal end of the container allowing air to vent from the container interior, a spacing member having a protruding portion extending from the distal end of the cap into the container interior, and a stopper slidably disposed within the container interior of the container, the stopper sized relative to the container to provide sealing engagement with the sidewall of the container, the stopper having a stopper distal end and a stopper proximal end. The blood collection cartridge further includes a first fluid reservoir located within the sidewall between the closure proximal end and the stopper distal end, a second fluid reservoir located within the sidewall between the cap distal end and the stopper proximal end, and an anticoagulant disposed within the first fluid reservoir, wherein the stopper is slidable between a distal position in which the stopper is adjacent the closure proximal end such that the anticoagulant completely fills the first fluid reservoir and a proximal position in which the stopper abuts the spacing member.

In one configuration, with the stopper in the distal position the second fluid reservoir is larger than the first fluid reservoir. In another configuration, with the stopper in the proximal position the first fluid reservoir is larger than the second fluid reservoir. In yet another configuration, the spacing member is connected to the distal end of the cap. In one configuration, the spacing member is integral with the cap.

In accordance with another embodiment of the present invention, a blood collection system includes a blood collection cartridge including a container having a distal end, a proximal end, and a sidewall extending therebetween and defining a container interior, a resealable closure sealing the distal end of the container, the resealable closure having a closure distal end and a closure proximal end, a cap sealing the proximal end of the container, the cap having a cap distal end and a cap proximal end, and a stopper slidably disposed within the container interior of the container, the stopper sized relative to the container to provide sealing engagement with the sidewall of the container, the stopper having a stopper distal end and a stopper proximal end. The blood collection cartridge further includes a first fluid reservoir located within the sidewall between the closure proximal end and the stopper distal end, a second fluid reservoir located within the sidewall between the cap distal end and the stopper proximal end, and an anticoagulant disposed within the first fluid reservoir. The blood collection system further includes a needle assembly including a translucent hub configured to provide a visual indication of flashback of a fluid flowing into the hub and at least one cannula having a cannula distal end and a cannula proximal end, a portion of the at least one cannula mounted within the hub. The blood collection system further includes a holder attached to the needle assembly, with the blood collection cartridge inserted within the holder and connected with the needle assembly such that the cannula proximal end pierces the closure of the blood collection cartridge, the first fluid reservoir of the blood collection cartridge and the at least one cannula of the needle assembly are in fluid communication.

In accordance with another embodiment of the present invention, a method of collecting a blood sample from a blood vessel includes: obtaining a blood collection assembly including a needle assembly and a holder attached to the needle assembly; inserting a distal end of the needle assembly into the blood vessel; obtaining a blood collection cartridge including: a container having a distal end, a proximal end, and a sidewall extending therebetween and defining a container interior; a resealable closure sealing the distal end of the container, the resealable closure having a closure distal end and a closure proximal end; a cap sealing the proximal end of the container, the cap having a cap distal end and a cap proximal end, the cap rotatable between a closed position in which the cap seals the proximal end of the container and an open position in which the cap breaks the seal with the proximal end of the container allowing air to vent from the container interior; a spacing member having a protruding portion extending from the distal end of the cap into the container interior; a stopper slidably disposed within the container interior of the container, the stopper sized relative to the container to provide sealing engagement with the sidewall of the container, the stopper having a stopper distal end and a stopper proximal end; a first fluid reservoir located within the sidewall between the closure proximal end and the stopper distal end; a second fluid reservoir located within the sidewall between the cap distal end and the stopper proximal end; and an anticoagulant disposed within the first fluid reservoir; inserting the blood collection cartridge into the holder such that blood flows into the first fluid reservoir and forces the stopper to travel in a proximal direction along a longitudinal axis of the container; removing the blood collection cartridge from the holder when the stopper contacts the spacing member; and removing the distal end of the needle assembly from the blood vessel.

In one configuration, the anticoagulant disposed within the first fluid reservoir is in a liquid form. In another configuration, the method further includes rotating the cap to the open position prior to or after insertion of the blood collection cartridge into the holder to allow air to vent from the container interior of the container. In yet another configuration, the method further includes rotating the cap to the closed position prior to the removal of the blood collection cartridge from the holder to seal the proximal end of the container of the blood collection cartridge. In one configuration, the method further includes attaching a luer adapter to the distal end of the container of the blood collection cartridge.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
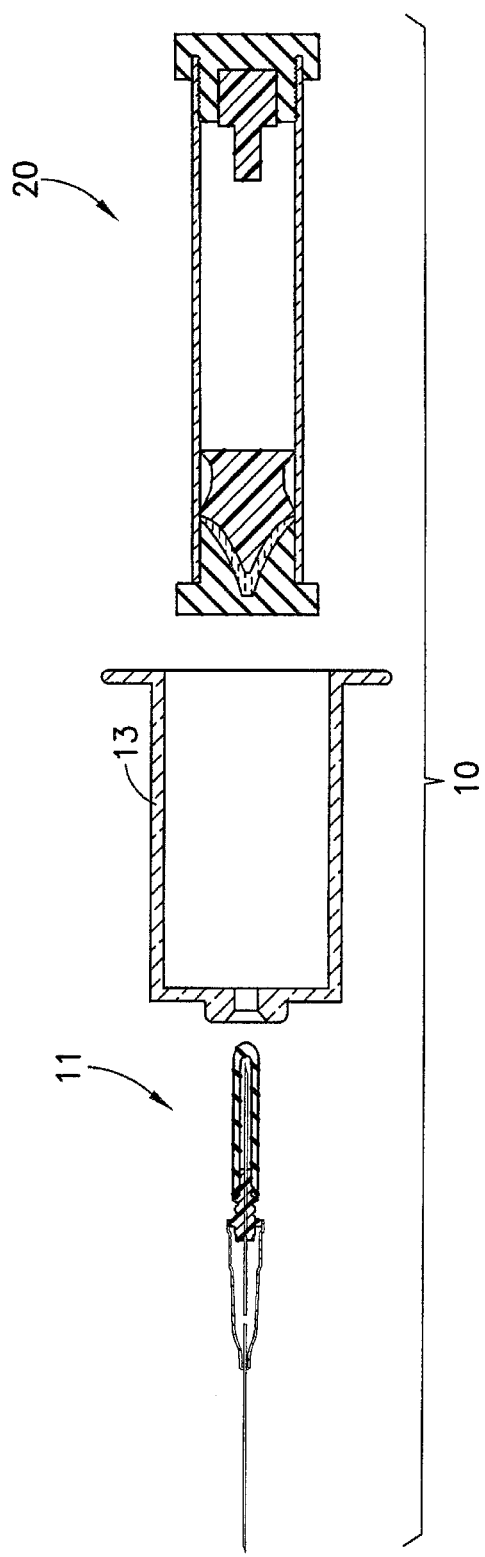
FIG. 1 is an exploded, cross-sectional view of a blood collection system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention. Before describing several exemplary embodiments of the invention, it is to be understood that the invention is not limited to the details of construction or process steps set forth in the following description and drawings. The invention is capable of other embodiments and of being practiced or carried out in various ways.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a location on the blood collection assembly of the present disclosure that is, during normal use, closest to a patient who is receiving treatment and farthest from a clinician administering the treatment to the patient and "proximal" refers to the opposite direction of distal, i.e., farthest from the patient who is receiving treatment and closest to the clinician administering the treatment to the patient. Furthermore, in the following discussion, "proximal direction" refers to a direction of movement away from the patient who is receiving treatment and toward the clinician administering the treatment to the patient, and "distal direction" refers to a direction of movement toward the patient who is receiving treatment and away from the clinician administering the treatment to the patient. For purposes of this disclosure, the above-mentioned references are used in the description of the components of a blood collection assembly in accordance with the present disclosure.

Referring to FIGS. 1-7 an arterial blood collection assembly or blood collection system 10 includes a needle assembly 11, a tube holder 13, and a blood collection cartridge 20. The present invention is generally described in terms of an arterial blood collection assembly 10. While described herein in terms of a preferred embodiment of an arterial blood collection cartridge 20 intended for use with a needle assembly 11, the cartridge 20 of the present disclosure may be used with or may incorporate other medical devices, such as another medical device assembly that includes a piercing element or allows for attachment to a catheter or arterial lines.

Figure 2:
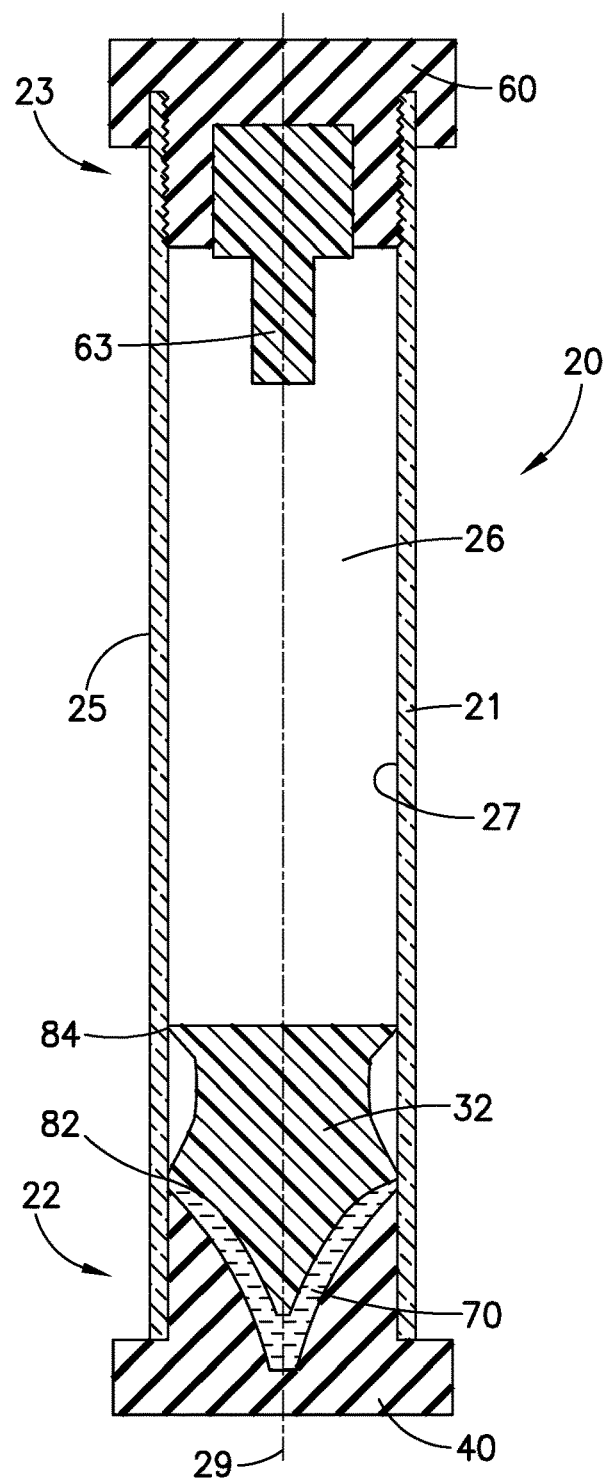
FIG. 2 is a cross-sectional view of a blood collection cartridge in accordance with an embodiment of the present invention.

Referring to FIGS. 1-4, arterial blood collection cartridge 20 include a closure 40, an anticoagulant 70, a stopper 32 that is slidably disposed within a container 21, a collection volume spacer or spacing member 63, and a cap 60. Referring to FIG. 2, blood collection cartridge 20 includes a tube or container 21 having an open distal end 22 and an opposing, open proximal end 23. Container 21 defines a container longitudinal axis 29. In one embodiment, tube 21 is an elongated, hollow, cylindrically-shaped container. In other embodiments, tube 21 may include other shapes and sizes. For example, tube 21 may have other multi-sided polygon cross-sectional shapes, such as square or rectangular cross-sectional shapes. Container 21 has a rigid tubular wall or sidewall 25 that defines an internal chamber or container interior 26 extending between distal end 22 and proximal end 23. The rigid tubular wall 25 of tube 21 defines an internal surface 27 for slidably receiving a low resistance stopper 32.

Tube 21 may be made of one or more than one of the following representative materials: polypropylene, polyethylene, polyethyleneterephthalate (PET), polystyrene, polycarbonate, cellulosics, glass products, or combinations thereof. More expensive plastics such as polytetrafluoroethylene and other fluorinated polymers may also be used. In addition to the materials mentioned above, examples of other suitable materials include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF, and perfluoroalkoxy resins. One exemplary glass product is PYREX® (available from Corning Glass, Corning, N.Y.). Ceramic collection devices can be used according to embodiments of the invention. Cellulosic products such as paper and reinforced paper containers can also be used to form collection devices according to the invention.

Figure 3:
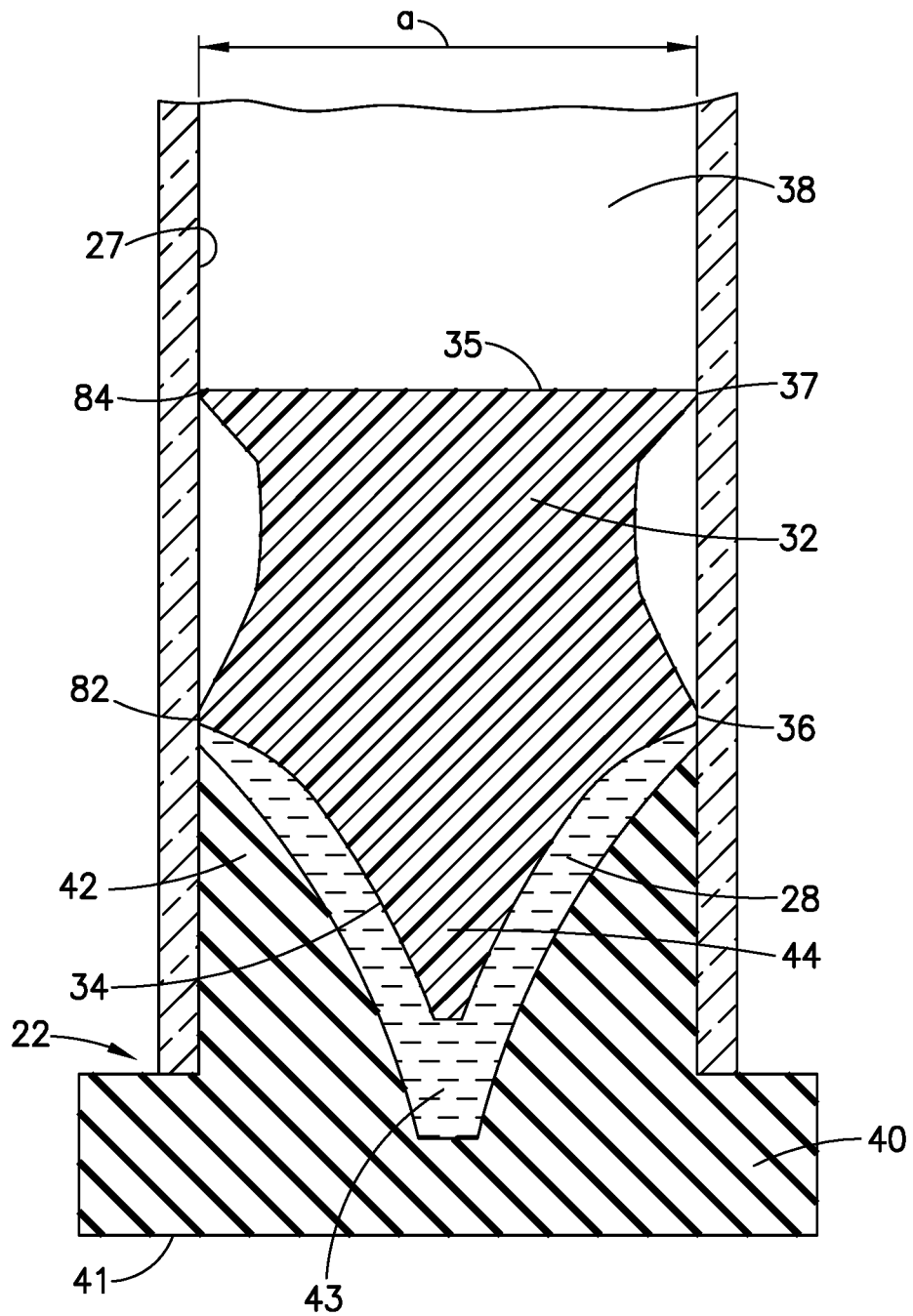
FIG. 3 is a fragmentary, cross-sectional view of the distal end of the blood collection cartridge of FIG. 2 in accordance with an embodiment of the present invention.
Figure 4:
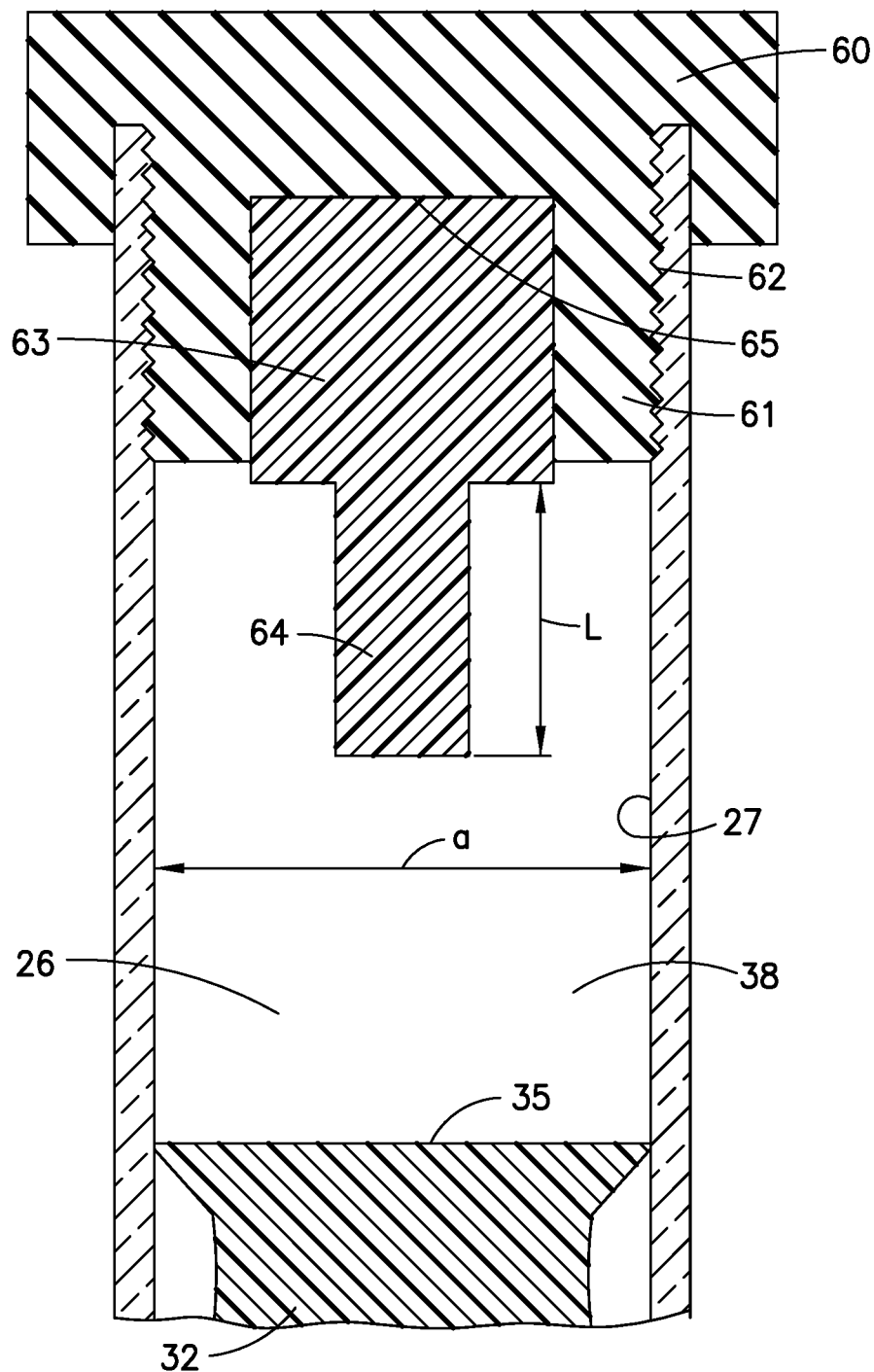
FIG. 4 is a fragmentary, cross-sectional view of the proximal end of the blood collection cartridge of FIG. 2 in accordance with an embodiment of the present invention.

Referring to FIGS. 2-4, arterial blood collection cartridge 20 includes a low resistance stopper 32 slidably received within the chamber 26 defined by tubular sidewall 25 of container 21. Stopper 32 is in sealing contact with the internal surface of sidewall 25 of container 21 and stopper 32 is slidably positioned in fluid tight engagement with internal surface 27, and is able to, slide distally and proximally along longitudinal axis 29 of container 21. Stopper 32 includes a distal face or stopper distal end 34 and opposing proximal face or stopper proximal end 35. The diameter of stopper 32 is approximately equal to or only slightly smaller than the internal diameter 'a' (FIG. 3) of container 21. Stopper 32 is in slidable contact with internal surface 27 of tube 21 and provides a fluid-tight seal with the internal surface 27 of the tube 21 so that a sample can be held within a fluid reservoir or first fluid reservoir 28 formed within the chamber 26 between distal end 22 of tube 21 and distal face 34 of stopper 32, thereby preventing the sample from leaking from the proximal end 23 of tube 21. In one embodiment, first fluid reservoir 28 is located within sidewall 25 between a proximal end of closure 40 and the distal end 34 of stopper 32. Stopper 32 is sized relative to container 21 to provide sealing engagement with the interior surface of sidewall 25 of container 21. In alternative embodiments, stopper 32 may include one or more annular ribs extending around the periphery of stopper 32 to increase the sealing engagement between stopper 32 and the interior surface of sidewall 25 of container 21. In other alternate embodiments, a singular O-ring or a plurality of O-rings may be circumferentially disposed about stopper 32 to increase the sealing engagement with the interior surface of sidewall 25.

Figure 7:
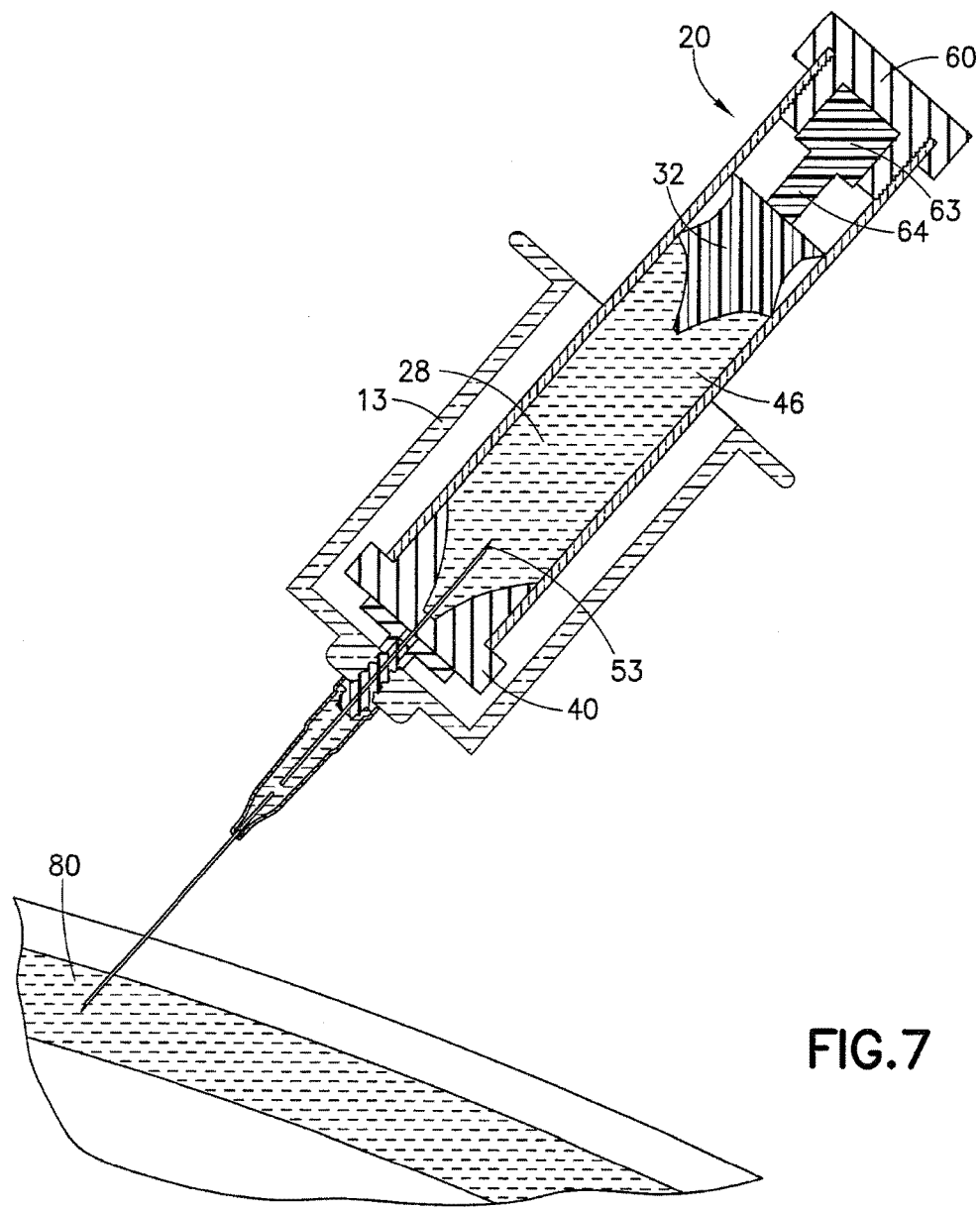
FIG. 7 is a cross-sectional view of the needle assembly and the holder of FIG. 6 with a blood collection cartridge inserted within the holder and in fluid communication with the needle assembly, upon completion of the collection of a blood sample from the artery, in accordance with an embodiment of the present invention.

Referring to FIGS. 3 and 7, stopper 32 is slidable between a distal position (FIG. 3) in which stopper 32 is adjacent a closure proximal end 42 such that anticoagulant 70 completely fills first fluid reservoir 28, and a proximal position (FIG. 7) in which stopper 32 abuts spacing member 63.

In some embodiments, stopper 32 is a low resistance stopper and as such is designed to have a relatively lower frictional resistance to movement inside of tube 21 when compared to similar components in prior art arterial blood gas syringes such that the presence of arterial blood pressure (approximately 100 to 160 mmHg) within fluid reservoir 28 will cause the stopper 32 to slide/travel in a proximal direction toward the proximal end 23 of tube 21 until the proximal face 35 contacts collection volume spacer 63 thereby limiting the proximal movement of stopper 32. The frictional resistance of a stopper can be lowered by either of a combination of stopper sealing profile design and/or component material selection.

Referring to FIG. 3, a first 36 sealing ring and a second 37 sealing ring extend around the outer circumferential surface of stopper 32 adjacent distal face 34 and proximal face 35 respectively to create a primary and secondary seal with internal surface 27 of tube 21. This stopper sealing profile design lowers the amount of contact between stopper 32 and internal surface 27 thereby reducing the frictional resistance to movement of stopper 32 when compared to a stopper sealing profile in which the entire outer circumferential surface is in contact with internal surface 27. Alternately or in combination with the stopper sealing profile design, stopper 32 is preferably made of an elastomeric material such as natural rubber, synthetic rubber, thermoplastic elastomers, and combinations thereof which are formulated or synthesized to be self-lubricating or have relatively lower frictional resistance. Stopper 32 may also be made from a combination of elastomers which include a harder inner rubber core and a soft self-lubricating polymeric material outer layer. A self-lubricating polymeric material has a lubricant incorporated into the polymeric material, an example of which is Epilor.

Referring to FIGS. 2 and 3, stopper 32 only contacts sidewall 25 of container 21 at a first point 82 and a second point 84 spaced from the first point 82. Importantly, no other portion of stopper 32 contacts sidewall 25 of container 21. In this manner, frictional resistance between stopper 32 and container 21, which restricts movement of stopper 32 within the container interior 26 of container 21, only exists at first point 82 and second point 84. Referring to FIG. 3, first point 82 where stopper 32 contacts sidewall 25 of container 21 includes first sealing ring 36 which creates a first seal with sidewall 25 of container 21. Referring again to FIG. 3, second point 84 where stopper 32 may also contact sidewall 25 of container 21 includes second sealing ring 37 which creates a second seal with sidewall 25 of container 21. In this manner, the contact area between stopper 32 and sidewall 25 of container 21 is reduced, thereby reducing the frictional resistance which restricts movement of stopper 32 within container 21.

Referring to FIGS. 2-4, stopper 32 is in slidable contact with internal surface 27 of tube 21 and provides a fluid-tight seal with the internal surface 27 of the tube 21 so that a sample can be held within a fluid reservoir or first fluid reservoir 28 formed within the chamber 26 between distal end 22 of tube 21 and distal face 34 of stopper 32, thereby preventing the sample from leaking from the proximal end 23 of tube 21. First fluid reservoir 28 is located within sidewall 25 between closure proximal end 42 and stopper distal end 34. A second fluid reservoir 38 is formed within the chamber 26 of container 21 and is located within sidewall 25 between the distal end of cap 60 and stopper proximal end 35. With stopper 32 in the distal position (FIGS. 2 and 3), the second fluid reservoir 38 is larger than the first fluid reservoir 28. With stopper 32 in the proximal position (FIG. 7), the first fluid reservoir 28 is larger than the second fluid reservoir 38.

Distal end 22 of tube 21 is sealed by closure 40 to form a liquid impermeable seal to contain the blood sample. The closure 40 includes an external end or closure distal end 41 and an internal end or closure proximal end 42 structured to be at least partially received within the tube 21. Portions of the closure 40 adjacent the open distal end 22 of the tube 21 define a maximum outer diameter which exceeds the inside diameter 'a' (FIGS. 3 and 4) of the tube 21. The inherent resiliency of closure 40 can ensure a sealing engagement with the internal surface 27 of the wall 25 of the tube 21. Portions of the closure 40 extending downwardly from the internal end 42 may taper from a minor diameter which is approximately equal to, or slightly less than, the inside diameter 'a' (FIGS. 3 and 4) of the tube 21 to a major diameter that is greater than the inside diameter 'a' of the tube 21 adjacent the distal end 22. Thus, the internal end 42 of the closure 40 may be urged into a portion of the tube 21 adjacent the distal open end 22. In an alternative embodiment, a luer lock feature can be incorporated to enhance the seal between the internal surface 27 of tube 21 and closure 40. Closure 40 is such that it can be pierced by a needle or other cannula to introduce a biological sample into tube 21 as is known in the art. Preferably, closure 40 is resealable. The closure 40 can also be formed to define at a cavity 43 extending into the internal end 42. The cavity 43 may be sized to receive at least a corresponding profile 44 extending distally from the distal face 34 of stopper 32. Suitable materials for closure 40 include, for example, elastomers such as silicone rubber, natural rubber, styrene butadiene rubber, ethylene-propylene copolymers and polychloroprene, and thermoplastic elastomers.

Proximal end 23 of tube 21 is sealed by a cap or twist cap 60 having mating screw threads located on the internal surface 27 of tube 21 and an outer surface 62 of an internal end 61 of cap 60 to form a liquid and gaseous impermeable seal when in the closed position. Rotating twist cap 60 in an anti-clockwise direction to an open position breaks the gaseous seal and allows air to escape or vent from chamber 26 proximal to stopper 32 into the surrounding atmosphere. This venting of air from chamber 26 eases the proximal movement of stopper 32 during the blood collection process as a back pressure is prevented from forming in chamber 26 between proximal face 35 of stopper 32 and twist cap 60. A back pressure in this location could prevent the collection of the intended volume of blood by prematurely retarding the proximal movement of stopper 32. Rotating twist cap 60 in a clockwise direction to the closed position, reforms a liquid and gaseous impermeable seal. In other words, cap 60 is rotatable between a closed position in which cap 60 seals the proximal end 23 of container 21 and an open position in which cap 60 breaks the seal with the proximal end 23 of container 21 allowing air to vent from the container interior 26 of container 21. In one embodiment, cap 60 has a cap distal end and an opposing, cap proximal end.

Collection volume spacer or spacing member 63 limits the proximal movement of stopper 32 thereby limiting the blood collection volume of container 21. The length 'L' (FIG. 4) that a projection or protruding portion 64 protrudes into chamber 26 can be designed to provide the desired blood collection volume of container 21. In current clinical practice, 2 ml of blood is collected for arterial blood gas analysis, therefore the length of protrusion 64 is preset such that when the proximal face 35 of stopper 32 contacts projection 64, a volume of 2 ml of blood is present within fluid reservoir 28 as shown in FIG. 7. Collection volume spacer 63 also maintains the position of stopper 32 during subsequent transportation and storage of the collected blood sample. Referring to FIGS. 1-4, collection volume spacer 63 is press-fitted into a recess 65 in the internal end 61 of twist-cap 60; however, collection volume spacer 63 and twist cap 60 may be connected by any method know in the art or may optionally be formed as a unitary or integral element.

According to an embodiment of the present disclosure, the arterial blood collection cartridge 20 may contain additional additives as required for particular testing procedures, such as anticoagulants, clotting agents, stabilization additives, and the like. Such additives may be sprayed onto the internal surface 27 of the tube 21 or located within fluid reservoir 28. The anticoagulants may include hirudins, hirudin derivatives, chelating agents, or chelating agent derivatives. Specific anticoagulants include citrate, ethylenediaminetetraacetic acid (EDTA), heparin, CPAD, CTAD, CPDA-1, CP2D, potassium oxalate, sodium fluoride, or ACD. The anticoagulant is used in a liquid form to improve the incorporation (hence, effectiveness) of the anticoagulant upon collection of arterial blood. The liquid form can be an emulsion, solution, or dispersion of the anticoagulant in a suitable carrier. Typically, prior art arterial blood sample collection methods use an arterial blood gas syringe pre-loaded upon manufacture with a solid form of anticoagulant such as heparin powder within the syringe barrel in order to maximize the shelf life of the syringe. The use of a solid form of anticoagulant can cause a reduction in the effectiveness of the anticoagulant as the incorporation of powdered heparin into the blood sample is difficult due to lack of agitation during the arterial blood collection process.

For the above reasons, first fluid reservoir 28 is completely filled with an anticoagulant 70 in liquid form (e.g., heparin) in order to remove any atmospheric air, so that the partial pressure of the oxygen in the arterial blood sample will not be affected by contact to any atmospheric air. The combination of cavity 43 in the internal end 42 of closure 40 and profile 44 extending from distal face 34 of stopper 32 provides a minimized "dead space" volume within fluid reservoir 28 prior to blood collection to minimize volume of liquid anticoagulant required to fill fluid reservoir 28, hence, minimize the dilution effect of the liquid heparin on the blood sample. In other words, as discussed above, when stopper 32 is located in the distal position (FIG. 3) in which stopper 32 is adjacent the closure proximal end 42, the anticoagulant 70 completely fills first fluid reservoir 28.

Referring to FIGS. 1 and 5-7, arterial blood collection system 10 includes a flashback needle assembly 11, a holder 13, and blood collection cartridge 20. Flashback needle assembly 11 could be a flashback needle assembly in accordance with the flashback needle assemblies described in U.S. Pat. No. 6,533,760, the entire disclosure of which is hereby expressly incorporated herein by reference.

Figure 5:
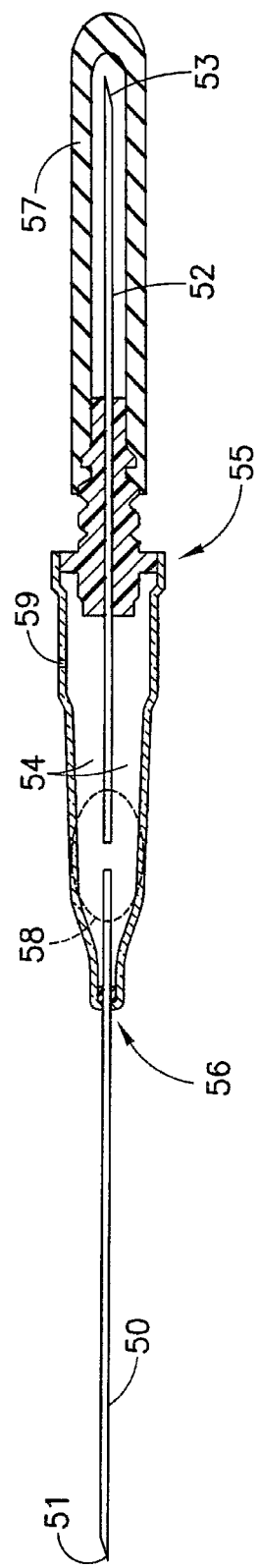
FIG. 5 is a cross-sectional view of a needle assembly in accordance with an embodiment of the present invention.

Referring to FIG. 5, needle assembly 11 includes a distal cannula 50 with a pointed distal end 51 and a proximal cannula 52 having a pointed proximal end 53 in axial alignment with one another to provide an axial fluid flow path 58 and each cannula having a lumen extending between the ends. The needle assembly 11 further comprises a clear/translucent hub 54 having a proximal end 55, a distal end 56, and a passage extending between the ends. Translucent hub 54 is configured to provide a visual indication of flashback of a fluid flowing into the hub 54. Both cannulas 50 and 52 are mounted securely in the passage of the hub 54. Thus, proximal end 53 of proximal cannula 52 projects proximally beyond the hub 54 and the pointed distal end 51 of distal cannula 50 projects distally beyond the hub 54. An external vent 59 through the wall of the plastic hub allows venting of air inside the distal cannula 50 and hub 54 which will be displaced by incoming blood. Flashback is produced when blood flows along the axial fluid flow path 58 between the two cannulas and provides visual confirmation of needle entry into the artery. External surface regions of the hub 54 near the proximal end 55 of the hub 54 may be formed with mounting structures, such as an array of external threads, at least one annular groove, or at least one annular rib. The mounting structure enables the needle hub 54 to be secured to a holder 13 that is configured to slidably receive a blood collection cartridge 20 according to an embodiment of the invention. The needle assembly 11 further includes a multiple sample sleeve 57 mounted over the proximal portions of the needle cannula 50 and secured to the proximal end 55 of the hub 54. The proximal portions of the needle cannula 50 and the multiple sample sleeve 57 project into the holder 13 when the hub 54 of the needle assembly 11 is mounted to the holder 13.

Assembly of the arterial blood collection cartridge 20 is accomplished by slidably inserting stopper 32 within chamber 26 through distal end 22 of tube 21. Liquid anticoagulant 70 such as heparin is then added to fill fluid reservoir 28 before distal end 22 is sealed by the insertion of closure 40. Collection volume spacer 63 is attached to twist cap 60 before twist cap 60 is screwed into the proximal end 23. The assembly can then be packaged for later use.

Figure 6:
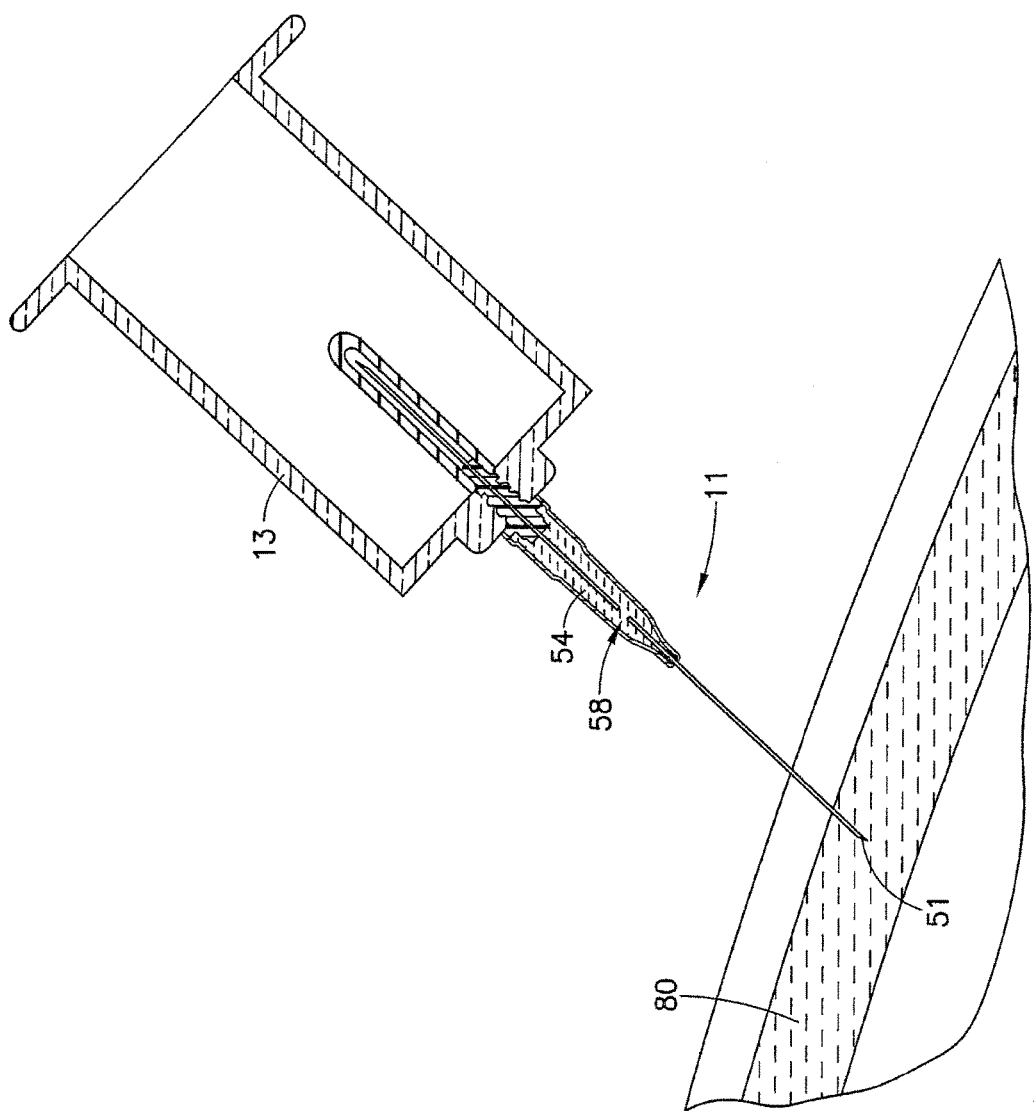
FIG. 6 is a cross-sectional view of the needle assembly of FIG. 5 attached to a holder and inserted into an artery in accordance with an embodiment of the present invention.

A method of blood collection according to an embodiment of this invention is described as follows. Needle assembly 11 is attached to holder 13. The user may then grip needle assembly 11 with holder 13 attached and insert pointed distal end 51 into an artery 80 of a patient. Blood at arterial pressure (which is greater than normal atmospheric or ambient pressure) will then flow through lumen of distal cannula 50 and into hub 54 via axial flow path 58 thereby providing visual indication of flashback confirming that distal end 51 is located in artery 80 as shown in FIG. 6. Blood collection cartridge 20 is then inserted in holder 13 such that pointed proximal end 53 of proximal needle 52 pierces multiple sample sleeve 57 and closure 40 once flashback is observed (i.e., blood is observed in hub 54).

Blood flows through the lumen into the fluid reservoir 28 and forces stopper 32 to slide in a proximal direction until the proximal face 35 of stopper 32 contacts projection 64 of collection volume spacer 63 thereby defining the completion of the collection volume of the blood sample as shown in FIG. 7. The sliding motion of the rubber stopper 32 allows the liquid anticoagulant 70 and collected arterial blood 46 to mix during the collection process. Twist cap 60 can be opened prior to insertion of the blood cartridge into the holder or during blood collection to allow air to vent from chamber 26 to further facilitate the proximal movement of stopper 32. Blood collection cartridge 20 is then removed from the multi-sample needle assembly 11 and holder 13 prior to the withdrawal of distal end 51 from the artery. The blood collection cartridge 20 containing the arterial blood sample is then ready for transportation to the laboratory for arterial blood gas analysis.

A luer adapter may then be inserted through closure 40 of the cartridge 20 to provide the cartridge with an interface connection that is compatible with a blood gas analyzer. A range of different luer adaptors can be provided to allow the arterial blood collection cartridge 20 to connect to all different types of the blood gas analyzer interfaces. The luer adaptor may also be supplied with a luer tip cap to seal the arterial blood collection cartridge 20 when the luer adapter is connected.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:
1. A blood collection cartridge, comprising:
a container having a distal end, a proximal end, and a sidewall extending therebetween and defining a container interior;
a resealable closure sealing the distal end of the container, the resealable closure having a closure distal end and a closure proximal end;
a cap sealing the proximal end of the container, the cap having a cap distal end and a cap proximal end, the cap transitionable between a closed position, in which the cap seals the proximal end of the container, and an open position, in which the cap breaks a liquid and gaseous impermeable seal with the proximal end of the container allowing air to vent from the container interior, the cap transitionable from the open position to the closed position to reform the liquid and gaseous impermeable seal with the proximal end of the container;
a stopper slidably disposed within the container interior of the container, the stopper sized relative to the container to provide sealing engagement with the sidewall of the container, the stopper having a stopper distal end and a stopper proximal end, wherein when the cap is in the open position, the cap allows the air to vent from the container interior to allow for movement of the stopper in the container interior of the container;
a first fluid reservoir located within the sidewall between the closure proximal end and the stopper distal end, wherein the first fluid reservoir is a fluid-tight reservoir formed by the sidewall, the closure proximal end, and the stopper distal end;

a second fluid reservoir located within the sidewall between the cap distal end and the stopper proximal end; and an anticoagulant disposed within at least one of the first fluid reservoir and the second fluid reservoir, wherein the stopper is configured to move toward the proximal end of the container due to a force caused by a pressure applied by fluid in the first fluid reservoir when the cap is in the open position, and to maintain a fluid-tight seal formed by the sidewall and the stopper distal end when moving toward the proximal end of the container such that the fluid remains contained in the first fluid reservoir.

2. The blood collection cartridge of claim 1, wherein the stopper contacts the sidewall of the container at a first point and a second point spaced from the first point, wherein no other portion of the stopper contacts the sidewall of the container.

3. The blood collection cartridge of claim 1, the stopper further comprising at least one sealing ring extending around an outer circumferential surface of the stopper.

4. The blood collection cartridge of claim 1, the stopper further comprising a first sealing ring and a second sealing ring each extending around an outer circumferential surface of the stopper.

5. The blood collection cartridge of claim 1, wherein the anticoagulant disposed within the first fluid reservoir is in a liquid form.

6. The blood collection cartridge of claim 1, wherein the cap comprises a spacing member having a protruding portion extending from the cap distal end into the container interior, wherein the spacing member is configured to limit proximal movement of the stopper within the container when the cap is engaged with the proximal end of the container and when the stopper moves to a proximal position adjacent the proximal end of the container based on the force caused by the pressure applied by the fluid in the first fluid reservoir, and wherein the spacing member is configured to maintain the stopper in the proximal position adjacent the proximal end of the container based on the force caused by the pressure applied by the fluid in the first fluid reservoir.

7. The blood collection cartridge of claim 6, wherein the spacing member is connected to the cap via a recess of the cap.

8. The blood collection cartridge of claim 6, wherein the cap is rotatable between the closed position in which the cap seals the proximal end of the container and the open position in which the cap breaks the liquid and gaseous impermeable seal with the proximal end of the container allowing the air to vent from the container interior.

9. The blood collection cartridge of claim 6, wherein the stopper is slidable to the proximal position, wherein the protruding portion of the spacing member extends along a container longitudinal axis of the container into the container interior without contacting the sidewall of the container to provide a predetermined collection volume within the first fluid reservoir when the stopper is in the proximal position, and wherein the stopper is configured to move toward the proximal end of the container.

10. A blood collection cartridge, comprising:

a container having a distal end, a proximal end, and a sidewall extending therebetween and defining a container interior;

a resealable closure sealing the distal end of the container, the resealable closure having a closure distal end and a closure proximal end;

a cap configured to seal the proximal end of the container, the cap having a cap distal end and a cap proximal end, the cap configured to be transitionable between a closed position, in which the cap seals the proximal end of the container, and an open position, in which the cap breaks a liquid and gaseous impermeable seal with the proximal end of the container allowing air to vent from the container interior, the cap configured to be transitionable from the open position to the closed position to reform the liquid and gaseous impermeable seal with the proximal end of the container;

a stopper configured to be slidably disposed within the container interior of the container, the stopper sized relative to the container to provide sealing engagement with the sidewall of the container, the stopper having a stopper distal end and a stopper proximal end, the stopper configured to contact the sidewall of the container at a first point and a second point spaced from the first point and no other portion of the stopper is configured to contact the sidewall of the container when the stopper is disposed within the container interior of the container, wherein when the cap is in the open position, the cap allows the air to vent from the container interior to allow for movement of the stopper in the container interior of the container;

a first fluid reservoir located within the sidewall between the closure proximal end and the stopper distal end, wherein the first fluid reservoir is a fluid-tight reservoir formed by the sidewall, the closure proximal end, and the stopper distal end; and a second fluid reservoir located within the sidewall between the cap distal end and the stopper proximal end, wherein the stopper is configured to move toward the proximal end of the container due to a force caused by a pressure applied by fluid in the first fluid reservoir when the cap is in the open position, and to maintain a fluid-tight seal formed by the sidewall and the stopper distal end when moving toward the proximal end of the container such that the fluid remains contained in the first fluid reservoir.

11. The blood collection cartridge of claim 10, further comprising an anticoagulant within the first fluid reservoir.

12. The blood collection cartridge of claim 10, wherein frictional resistance between the stopper and the container, which restricts movement of the stopper in the container interior of the container, only exists at the first point and the second point.

13. The blood collection cartridge of claim 10, wherein the first point of the stopper comprises a first sealing ring which creates a first seal with the sidewall of the container.

14. The blood collection cartridge of claim 13, wherein the second point of the stopper comprises a second sealing ring which creates a second seal with the sidewall of the container.

15. A blood collection cartridge, comprising:

a container having a distal end, a proximal end, and a sidewall extending therebetween and defining a container interior;

a resealable closure sealing the distal end of the container, the resealable closure having a closure distal end and a closure proximal end;

a cap sealing the proximal end of the container, the cap having a cap distal end and a cap proximal end, the cap rotatable between a closed position in which the cap seals the proximal end of the container and an open position in which the cap breaks a liquid and gaseous impermeable seal with the proximal end of the container allowing air to vent from the container interior, the cap transitionable from the open position to the closed position to reform the liquid and gaseous impermeable seal with the proximal end of the container;

a spacing member having a protruding portion extending from the cap distal end along a container longitudinal axis of the container into the container interior;

a stopper slidably disposed within the container interior of the container, the stopper sized relative to the container to provide sealing engagement with the sidewall of the container, the stopper having a stopper distal end and a stopper proximal end, wherein when the cap is in the open position, the cap allows the air to vent from the container interior to allow for movement of the stopper in the container interior of the container;

a first fluid reservoir located within the sidewall between the closure proximal end and the stopper distal end, wherein the first fluid reservoir is a fluid-tight reservoir formed by the sidewall, the closure proximal end, and the stopper distal end;

a second fluid reservoir located within the sidewall between the cap distal end and the stopper proximal end; and an anticoagulant disposed within the first fluid reservoir, wherein the stopper is slidable between a distal position in which the stopper is adjacent the closure proximal end such that the anticoagulant completely fills the first fluid reservoir and a proximal position in which the stopper abuts the spacing member, wherein the stopper is configured to move toward the proximal end of the container due to a force caused by a pressure applied by fluid in the first fluid reservoir when the cap is in the open position, and to maintain a fluid-tight seal formed by the sidewall and the stopper distal end when moving toward the proximal end of the container such that the fluid remains contained in the first fluid reservoir.

16. The blood collection cartridge of claim 15, wherein with the stopper in the distal position the second fluid reservoir is larger than the first fluid reservoir.

17. The blood collection cartridge of claim 15, wherein with the stopper in the proximal position the first fluid reservoir is larger than the second fluid reservoir.

18. The blood collection cartridge of claim 15, wherein the spacing member is connected to the cap distal end.

19. The blood collection cartridge of claim 15, wherein the spacing member is integral with the cap.

20. A blood collection system, comprising:
a blood collection cartridge, comprising:
    a container having a distal end, a proximal end, and a sidewall extending therebetween and defining a container interior,
    a resealable closure sealing the distal end of the container, the resealable closure having a closure distal end and a closure proximal end,
    a cap sealing the proximal end of the container, the cap having a cap distal end and a cap proximal end, the cap transitionable between a closed position, in which the cap seals the proximal end of the container, and an open position, in which the cap breaks a liquid and gaseous impermeable seal with the proximal end of the container allowing air to vent from the container interior, the cap transitionable from the open position to the closed position to reform the liquid and gaseous impermeable seal with the proximal end of the container,
    a stopper slidably disposed within the container interior of the container, the stopper sized relative to the container to provide sealing engagement with the sidewall of the container, the stopper having a stopper distal end and a stopper proximal end, wherein when the cap is in the open position, the cap allows the air to vent from the container interior to allow for movement of the stopper in the container interior of the container,
    a first fluid reservoir located within the sidewall between the closure proximal end and the stopper distal end, wherein the first fluid reservoir is a fluid-tight reservoir formed by the sidewall, the closure proximal end, and the stopper distal end,
    a second fluid reservoir located within the sidewall between the cap distal end and the stopper proximal end, and
    an anticoagulant disposed within the first fluid reservoir;
a needle assembly, comprising:
a hub configured to provide a visual indication of flashback of a fluid flowing into the hub, and
    at least one cannula having a cannula distal end and a cannula proximal end, a portion of the at least one cannula mounted within the hub; and
a holder attached to the needle assembly, such that with the blood collection cartridge inserted within the holder and connected with the needle assembly the cannula proximal end pierces the resealable closure of the blood collection cartridge, thereby providing the first fluid reservoir and the at least one cannula in fluid communication,
wherein the stopper is configured to move toward the proximal end of the container due to a force caused by a pressure applied by the fluid in the first fluid reservoir when the cap is in the open position, and to maintain a fluid-tight seal formed by the sidewall and the stopper distal end when moving toward the proximal end of the container, such that the fluid remains contained in the first fluid reservoir.

21. The blood collection system of claim 20, further comprising a spacing member having a protruding portion extending from the cap distal end into the container interior, wherein the spacing member is press-fitted into a recess of the cap.

* * * * *